(12) United States Patent
Thorsted (10) Patent No.: US 12,350,429 B2
(45) Date of Patent: Jul. 8, 2025

(54) MEDICAL SUCTION DEVICES AND USES THEREOF

(71) Applicant: Sipka Medical Solutions LLC, Redding, CA (US)

(72) Inventor: Richard Thorsted, Vacaville, CA (US)

(73) Assignee: Sipka Medical Solutions LLC, Redding, CA (US)

( * ) Notice: Subject to any disclaimer, the term of this patent is extended or adjusted under 35 U.S.C. 154(b) by 153 days.

(21) Appl. No.: 16/888,292

(22) Filed: May 29, 2020

(65) Prior Publication Data

US 2021/0369999 A1 Dec. 2, 2021

(51) Int. Cl.
*A61M 16/04* (2006.01)
*A61M 1/00* (2006.01)

(52) U.S. Cl.
CPC ........ *A61M 16/0463* (2013.01); *A61M 1/682* (2021.05); *A61M 1/774* (2021.05); *A61M 16/0402* (2014.02); *A61M 16/0477* (2014.02); *A61M 2205/586* (2013.01)

(58) Field of Classification Search
CPC .......... A61M 16/0463; A61M 16/0402; A61M 16/0477; A61M 1/774; A61M 1/682; A61M 2205/586
See application file for complete search history.

(56) References Cited

U.S. PATENT DOCUMENTS

| | | | |
|---|---|---|---|
| 1,805,471 A | 5/1931 | England | |
| 3,572,340 A | 3/1971 | Lloyd et al. | |
| 3,742,952 A | 7/1973 | Magers et al. | |
| 4,525,166 A | 6/1985 | Leclerc | |
| 6,036,672 A * | 3/2000 | Allen | A61M 39/20 604/167.02 |
| 6,129,547 A | 10/2000 | Cise | |
| 8,834,408 B2 | 9/2014 | Baker | |
| 9,603,981 B2 | 3/2017 | Lathim | |
| 2003/0145849 A1 * | 8/2003 | Drinan | A61M 3/0262 128/200.14 |

(Continued)

FOREIGN PATENT DOCUMENTS

CN 209392474 9/2019

OTHER PUBLICATIONS

"APC985015 V-Vac Complete Starter Kit", https://allamericanswim.com/american-pools-corporation-vvac-complete-starter-kit.html (Accessed online Aug. 28, 2020).

(Continued)

*Primary Examiner* — Rebecca E Eisenberg
*Assistant Examiner* — Rachel O'Connell
(74) *Attorney, Agent, or Firm* — Rudy J. Ng; Michael J. Blessent; Bozicevic, Field & Francis LLP (57) ABSTRACT

Provided is a medical suction device including a compressible object including a surface, an opening in the surface, and a lumen defined by the surface and the opening, along with a tubular member located inside the compressible object. Also provided is a medical suction apparatus including the medical suction device and a catheter dimensioned to fit inside the tubular member of the device. A method of removing liquid from the throat of a subject using the medical suction apparatus is also provided, as well as kits including the medical suction device.

25 Claims, 7 Drawing Sheets

(56) References Cited

U.S. PATENT DOCUMENTS

| | | | | |
|---|---|---|---|---|
| 2007/0027433 | A1* | 2/2007 | Garcia | A61M 1/82 |
| | | | | 604/319 |
| 2009/0187195 | A1* | 7/2009 | Berk | A61B 17/22031 |
| | | | | 606/127 |
| 2009/0281483 | A1* | 11/2009 | Baker | A61M 3/0212 |
| | | | | 604/35 |
| 2013/0165849 | A1* | 6/2013 | Monty | A61M 1/774 |
| | | | | 604/181 |
| 2015/0217041 | A1* | 8/2015 | Monty | A61M 3/0279 |
| | | | | 604/207 |
| 2015/0352303 | A1* | 12/2015 | Godwin | A61M 16/208 |
| | | | | 128/205.13 |
| 2016/0361078 | A1* | 12/2016 | Pagliacci | A61M 1/84 |
| 2018/0369526 | A1* | 12/2018 | McGowan | A61M 16/0463 |
| 2019/0091434 | A1* | 3/2019 | Reddy | A61M 39/02 |
| 2020/0046272 | A1 | 2/2020 | Brister et al. | |
| 2020/0368404 | A1 | 11/2020 | Park et al. | |

OTHER PUBLICATIONS

"LINE2design Portable Manual Suction Pump Hand Operated Vacuum Pump", https://www.line2ems.com/products/manual-suction-pump (Accessed online Aug. 28, 2020).

"Tactical Suction Device | North American Rescue", https://www.narescue.com/nar-tactical-suction-device.html (Accessed online Aug. 28, 2020).

* cited by examiner

MEDICAL SUCTION DEVICES AND USES THEREOF

INTRODUCTION

Proper medical treatment of a subject sometimes involves removing liquid from a body cavity of the subject. For example, if the torso, neck, or head of a subject is injured, liquids such as blood might begin to drain into the throat of the subject, inhibiting proper breathing. If the subject has a nervous system condition or injury that inhibits swallowing, liquids such as saliva might start to accumulate in the throat of the subject, also inhibiting breathing. In such cases, medical treatment typically involves removing such liquids from the throat.

Medical suction devices use a source of vacuum to aspirate and remove liquids from the throat. However, conventional systems are typically large, with many different components, and only located inside a hospital or medical clinic.

SUMMARY

Provided is a medical suction device including a compressible object comprising a surface, an opening in the surface, and a lumen defined by the surface and the opening, along with a tubular member located inside the compressible object. Also provided is a medical suction apparatus including the medical suction device and a catheter dimensioned to fit inside the tubular member of the device. A method of removing liquid from the throat of a subject using the medical suction apparatus is also provided, as well as kits including the medical suction device.

DETAILED DESCRIPTION

Provided is a medical suction device including a compressible object comprising a surface, an opening in the surface, and a lumen defined by the surface and the opening, along with a tubular member located inside the compressible object. Provided is a medical suction apparatus including a medical suction device and a catheter dimensioned to fit inside the tubular member of the device. A method of removing liquid from the throat of a subject using a medical suction apparatus is also provided, as well as kits including the medical suction device.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets and reference to "the discrete entity" includes reference to one or more discrete entities, and so forth.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the definition or usage of any term herein conflicts with a definition or usage of a term in an application or reference incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The terms "opening" and "hole" are used interchangeably herein. For clarity, the term opening is usually used in the context of the compressible object, whereas the term hole is usually used in the context of the tubular member.

The terms "tubular member" and "dual through-hole element" are used interchangeably herein.

Devices

A medical suction device includes a compressible object comprising a surface, an opening in the surface, and a lumen defined by the surface and the opening, along with a tubular member located inside the compressible object. The tubular member has a first end, a middle section, and a second end. The first end has a first hole located at the opening of the compressible object, and the second end has a second hole. The lumen of the compressible object is in fluid communication with a space outside the compressible object through the tubular member.

Compressible Object

As used herein, compressible means that when a force is exerted on the object, the object changes shape so that the volume of the space inside the object (i.e. the volume of the lumen) decreases.

The object can have a variety of three-dimensional shapes. Overall, the compressible object can have any suitable shape provided that it encloses a volume (i.e. the lumen) and it allows for the inclusion of an opening in the surface of the object.

For example, the object can have a shape that is exactly or approximately an ellipsoid, a sphere, a spheroid, a cylinder, a cone, a cube, a cuboid (i.e. 3-dimensional rectangle), a closed hyperboloid of one sheet, and a three-dimensional polyhedron. The shape can have 90° angles or rounded edges. The object can also have a shape that resembles existing objects, such as an American football, a Rugby ball, a barbell, a pear, a watermelon, an olive, an egg, a banana, or a light bulb. Exemplary light bulb shapes include A19, B13, C15, S14, R40, G30, T9, and BT56.

The equation shown below can be used to describe a sphere, a spheroid, and an ellipsoid. A, b, and c are constants whereas x, y, and z are variables corresponding to the three Cartesian coordinates (x, y, z).

$$\frac{x^2}{a^2} + \frac{y^2}{b^2} + \frac{z^2}{c^2} = 1$$

If a=b=c, then a sphere is generated. When two of the constants (e.g. a and b) are the same but the third constant (e.g. c) is different, then a spheroid is generated. An oblate spheroid results when the two equal constants are larger than the unequal constant (e.g. a=b>c). A prolate spheroid results when the two equal constants are smaller than the unequal constant (e.g. a=b<c). When the three constants are unequal (a≠b≠c), then an ellipsoid is generated.

For example, an American football is approximately a prolate spheroid in shape. In particular, the football has a length (2c) that is longer than its width (2a) and height (2b). Since the width and height are the same, a cross-section perpendicular to the length of the football is a circle. At the same time, a cross-section parallel to the length of the football is an oval.

For the compressible objects described herein, some can be exactly prolate spheroid in shape. However, they can also be approximately prolate spheroid in shape. For example, instead of having perfectly oval cross-sections, the object might have cross-sections more similar to a square with rounded edges. An egg, such as a chicken egg, and a watermelon are examples of objects that are approximately prolate spheroidal in shape.

Similarly, the compressible object can have a cylindrical shape. In some cases, the object has a perfectly cylindrical shape, i.e. perfectly circular cross-sections and perfect 90° angles at each end. In other cases, the compressible object can be approximately cylindrical, e.g. with rounded cross-sections that are approximately oval in shape and ends that have rounded edges rather than perfect 90° angles. In addition, with an approximate cylinder, the ends can be curved instead of being a perfectly flat plane. The ends can either curve outwards or inwards.

In some cases, object can be thinner at one end and wider at the other end. A cone shape is one example of such an embodiment. Typically the opening is located at the thinner end.

In some cases, the object can be wider at either ends while being thinner in the middle. A hyperboloid of one sheet is one example of such a shape. In certain cases, this object starts thin at one end, becomes thicker, becomes thinner, becomes thicker, and finally ends thinner. This embodiment is sometimes called a barbell-shape after metal object used by athletes for increasing muscle mass.

The compressible object can also be irregularly shaped such that it is not rotationally symmetrical. For example, a banana is approximately cylindrical in shape, but it is also curved along its length and the curvature at its two ends is not identical.

The compressible object can also have an approximately spherical section connected to a narrower section, such as with a G30-shaped light bulb.

The compressible object can also be any suitable three-dimensional polyhedron, with or without rounded edges. The object can be a cube, i.e. a 6-sided polyhedron having 6 equally-sized square faces. The 3-D polyhedron can also have irregularly shaped faces with different sizes and 2-D shapes.

Overall, the compressible object can have any suitable shape provided that it encloses a volume (i.e. the lumen) and it allows for the inclusion of an opening in the surface of the object.

For example, in some cases the object is approximately prolate spheroidal in shape and the opening is located at one end of prolate spheroid. In other words, a prolate spheroid has one dimension that is longer than the other two dimensions. The opening can be located where the axis of this longer dimension intersections with the surface of the spheroid. Regarding the example of an American football, the opening can be located at one of the tips of the football. In other cases, the opening can be located on a side of the football, i.e. not at a tip of the football.

In some cases, the compressible object has a shape that is approximately an ellipsoid, sphere, spheroid, cylinder, cone, cube, or cuboid.

As described above, the compressible object has a surface, which can also be referred to as a wall of the compressible object. Compressing and releasing the object can generate a suction force that can be used to suck gases or liquids into the lumen of the object. Suction force is used interchangeably with vacuum force, and suck is used interchangeably with aspirate.

When no force is being applied to the object, the object can have a first shape. Upon application of a compressive force, the object can move into a second shape, wherein the volume of the lumen decreases. Next, the compressive force can be released, causing the object to return at least partially to the first shape, e.g. completely to the first shape, thereby increasing the volume of the lumen. By causing this increase in volume, a suction force is generated at the opening that can aspirate gases and liquid into the lumen of the object. The magnitude of this suction force will depend upon how quickly the lumen increases in volume, the cross-sectional area of the opening, and other aspects of fluid dynamics. As such, a faster change from the second shape to the first shape will cause a larger suction force. In turn, the speed of this shape change depends on the original shape of the object and the material of the object, such as its hardness and stiffness. In some cases, the compressible object comprises a wall having a Shore indentation hardness ranging from 40 to 100, such as 50 to 90, or 60 to 80, as measured by the ASTM D2240 type A scale. In some cases, compressing one side of the compressible object by 25% along an axis perpendicular to the tubular member results in a stiffness ranging from 0.5 pounds per inch to 5.0 pounds per inch, such 1 to 4 or 2 to 3.

In some cases, the surface of the object includes plastic, rubber, or a combination thereof. In some cases, the compressible object and the tubular member are one piece, i.e., they are made of a single material. For example, the entire device can be formed or 3D printed as a single piece. In some cases, the compressible object can be elastically compressed along an axis perpendicular to the tubular member until it touches the tubular member without resulting in plastic deformation.

In some cases, the volume of the compressible object ranges from 10 ml to 500 ml, such as from 25 ml to 400 ml. In some cases, the volume is 10 ml or more, such as 25 ml or more, or 50 ml or more. In some cases, the volume is 500 ml or less, such as 250 ml or less. In some cases, the compressible object has a length ranging from 5 cm to 50 cm, such as from 10 cm to 40 cm. In some cases, the compressible object has a length of 50 cm or less, such as 40 cm or less. In some cases, the compressible object has a width (diameter) ranging from 2 cm to 20 cm, such as from 4 cm to 15 cm. In some cases, the ratio of the length to the width ranges from 0.5 to 6.0, such as from 0.9 to 3.0. In some cases, the compressible object has a wall having a thickness ranging from 0.05 cm to 0.5 cm.

These dimensions of the compressible object provide the advantage of making the device able to easily packed into a bag without occupying large amounts of space in the bag. In addition, the dimensions are small enough so that the object can be held and compressed by a single human hand, while also being large enough to allow aspiration of a significant amount of liquid into the device.

Tubular Member

The tubular member is located inside the compressible object and has a first end, a middle section, and a second end. The first end has a first hole located at the opening and the second end has a second hole. The lumen inside the compressible object is in fluid communication with a space outside the compressible object through the tubular member. The tubular member has a tubular member lumen extending from the first hole at the first end to the second hole at the second end. Tubular member is used interchangeably herein with the term "dual through-hole element".

The tubular member can have a variety of shapes. In some cases, the tubular member is exactly or approximately cylindrical in shape, wherein the holes and ends are located at the opposite ends of the cylinder. As such, the tubular member will have a circular cross-section. Each hole can encompass either a part or an entirety of the end. In other cases, the tubular member is similar to a cylinder, except that it has an oval or similarly curved cross-sectional area. In some cases, the tubular member can be similar to a cylinder, with the exception that the edges are rounded.

In other embodiments, the tubular member can be an exact or approximate cuboid (i.e. 3-dimensional rectangle). As such, the tubular member will have a square or rectangular cross-section. In such cases, the ends and holes are located at opposite faces of the cuboid.

In some cases, an interior surface of the middle section adjacent to the second hole comprises one or more ribs dimensioned to receive and hold a ribbed tip of a catheter. In other cases, an interior surface of the middle section adjacent to the second hole comprises threading dimensioned to receive and hold a threaded tip of a catheter. In still other cases, the middle section is dimensioned and configured to receive and hold a catheter through friction.

In some cases, the opening and the first end are connected with an air-tight and water-tight seal that includes the entire perimeter of the first hole. In some cases, the only fluid communication between the space inside the compressible object and the space outside the compressible object is through the tubular member and the opening. In other cases, there is fluid communication between the space inside the compressible object and the space outside the compressible object not only through the tubular member and the opening, but also through a second opening in the compressible object. For example, there can be a second opening in the compressible object that is directly adjacent to the reservoir. In such a case, the (first) opening and the second opening in the compressible object can be considered as through-holes. In some cases, the second opening is initially closed, but can be opened in order to drain liquid from the space inside the compressible object.

The tubular member can be located entirely inside the compressible object. In other cases, the first end of the tubular member is located partially outside the compressible object. For example, 10% to 90% of the length of the tubular member can be located outside the tubular member, such as 20% or 80% or 30% to 70%.

In cases where the tubular member is located entirely within the compressible object, the length of the tubular member is less than the length of the compressible object. As such, there is a gap between the second end of the tubular member and the compressible object. In some cases, the length of the tubular member ranges from 10% to 95% of the distance from the opening to an opposite side of the compressible object, such as from 20% to 80%. In some cases, such a distance is 25% or more, such as 50% or more. In some cases, the length of the tubular member ranges from 2 cm to 25 cm, such as from 4 cm to 20 cm. In some cases, the length is 2 cm or more, such as 5 cm or more. The inner diameter of the tubular member can range from 0.5 cm to 4 cm, such as from 1 cm to 2.5 cm.

Reservoir

In some cases, the compressible object has a reservoir that is the space located between the compressible object, the middle section, and a plane containing the second hole and oriented perpendicular to the tubular member.

In some cases, 25% to 95% of the volume inside the compressible object is located inside the reservoir, such as 35% to 90%. In some cases, 25% or more of the volume inside the compressible object is located inside the reservoir, such as 50% or more or 75% or more. In some cases, 95% or less of the volume inside the compressible object is located inside the reservoir, such as 75% or less or 50% or less.

In some cases, the reservoir has a volume ranging from 10 ml to 750 ml, such as from 50 ml to 500 ml, or from 75 ml to 400 ml. In some cases, the reservoir has a volume of 10 ml or more, such as 50 ml or more, or 100 ml or more. In some cases, the reservoir has a volume of 500 ml or less, such as 350 ml or less.

Additional Aspects

In some cases, the compressible object has a wall that is at least partially transparent, e.g. so that a user can visually determine whether and how much liquid is present inside the compressible object. In some cases, the wall can have markings that indicate the volume of liquid present within the compressible object, e.g. within the reservoir when the device is held in a certain orientation. Markings can be in any convenient unit, such as milliliters, fluid ounces, tablespoons, or drams.

In some cases, the device does not include a valve.

Apparatuses

Medical suction apparatuses include a medical suction device, as described in the preceding section, along with a catheter. The catheter has a distal end, along with a proximal end dimensioned to fit inside the tubular member of the suction device.

In some cases, one or more ribs located on an interior surface of the middle section and one or more ribs located on the proximal end of the catheter are dimensioned such that contact between the ribs will maintain the catheter inside the tubular member. In other cases, threading located on an interior surface of the middle section and threading located on the proximal end of the catheter are dimensioned such that contact between the threadings will maintain the catheter inside the tubular member.

In some case, the connection between the compressible object and the catheter is air-tight and water-tight.

In some cases the catheter is curved. In some cases, the catheter has a bulbous tip, e.g. a bulbous tip at the distal end. As used herein, the terms bulbous tip and Yankauer tip are used interchangeably.

Methods

Provided are methods of removing liquid from a throat of a subject, including:
(i) positioning a medical suction apparatus according to any of the preceding claims such that the distal end of the catheter is in contact with the liquid to be aspirated;
(ii) compressing the compressible object; and
(iii) releasing the compression on the compressible object, thereby aspirating at least some of the liquid from the throat into the compressible object.

In the above methods, releasing the compression on the compressible object creates a suction force that causes the aspiration of the liquid. When no force is being applied to the object, the object can have a first shape. Upon application of a compressive force, the object can move into a second shape, wherein the volume of the lumen decreases. Next, the compressive force can be released, causing the object to return at least partially to the first shape, e.g. completely to the first shape, thereby increasing the volume of the lumen. By causing this increase in volume, a suction force is generated at the opening that can aspirate gases and liquid into the lumen of the object. The magnitude of this suction force will depend upon how quickly the lumen increases in volume, the cross-sectional area of the opening, and other aspects of fluid dynamics. In some cases, releasing compression on the compressible object generates 10-500 mmHg of suction force at the opening, such as 25-400 mmHg, for example 50-200 mmHg.

In some cases, the compressing is performed before the positioning. In some cases, the compressing is performed during or after the positioning.

In some cases, the compressing, releasing, and positioning of is performed by a single human hand. In some cases, the compression is along an axis perpendicular to the tubular member. First, the compressing and releasing can be performed by contracting and relaxing the finger of the single human hand. In addition, by manipulating the position of the compressible object with the single hand, the user can also position and reposition the distal end of the catheter in the throat of the subject. Hence, the user's second hand is free to perform any other task, such as applying pressure to a bleeding wound or operating a radio or cell phone.

In some cases, the compressing and releasing is performed by a single human hand, wherein the second human hand can be used to position, hold, and orient the catheter. In other words, although the distal end of the catheter can be positioned indirectly by moving the compressible member with the first hand, using the second hand allows for potentially faster and more accurate positioning of the distal end in the throat.

In some embodiments, the method further includes: (iv) compressing and releasing the compressible object a second time to aspirate additional liquid from the throat into the compressible object, where the distal end of the catheter remained within the throat between the first releasing and the second compressing. The advantages of using the presently described apparatus without removing the catheter from the throat can be understood by considering an identical procedure, but using a simple pipette instead of the presently described apparatus. If using a simple pipette, the first releasing would aspirate liquid from the throat and into the pipette. However, the second compressing would then expel that same liquid from the pipette back into the throat. In other words, when using a simple pipette, repeated compression and releasing steps would merely cycle the liquid between the throat and the pipette, and no liquid would be removed. In order to avoid this problem, the pipette user would need to remove the pipette from the throat after the first releasing and then expel the liquid to another location, e.g. a waste receptacle, by performing the second compressing. Afterwards, the pipette user would then need to reinsert and reposition the pipette at the correct location within the throat. In other words, if using a simple pipette, the additional steps of removing and reinserting the pipette into the throat would be required for each aspiration of liquid, consuming the time and attention of the user. In contrast, the present apparatus allows for continuous, repeated aspirations of liquid from the throat without the need to remove the catheter from the throat. This advantage is achieved because, due to the position of the tubular member within the compressible object, the aspirated liquid becomes trapped in the reservoir where it cannot be readily expelled.

In some cases, the distal end of the catheter was repositioned within the throat between the first releasing and the second releasing. For example, once a volume of liquid is aspirated during a first releasing, the surface of the liquid in the throat might become lower. Therefore, the distal end of the catheter might need to be moved lower in the throat in order to maintain contact with the liquid in the throat.

In some cases, the liquid is blood, mucus, saliva, or a combination thereof.

In some cases, the compressing results in a 10% to 90% decrease in the volume of the compressible object, such as 20% to 80% or 30% to 70%.

Kits

Kits are provided that include a medical suction device as described previously, along with packaging containing the medical suction device. In some cases the kit also includes a catheter. The catheter can be curved. The catheter can have a Yankauer tip. The kit can also include instructions specifying how to use the device, e.g. the instructions can list the method described above. In some cases, the medical suction device, and catheter if present, is sterile and the packaging is configured to keep the medical suction device sterile.

Notwithstanding the appended claims, the disclosure is also defined by the following clauses:

1. A medical suction device, comprising:
   a compressible object comprising a surface, an opening in the surface, and an internal lumen defined by the surface and the opening,
   a tubular member located inside the compressible object and comprising a first end, a middle section and a second end,
   wherein the first end comprises a first hole located at the opening and the second end comprises a second hole,
   wherein the lumen of the compressible object is in fluid communication with a space outside the compressible object through the tubular member.

2. The device of clause 1, wherein the compressible object comprises a reservoir comprising a space located between the surface of the compressible object, the middle section, and a plane containing the second hole and oriented perpendicular to the tubular member.

3. The device of clause 2, wherein the reservoir has a volume ranging from 10 ml to 750 ml.

4. The device of any one of clauses 1-3, wherein 25% to 95% of the volume of the lumen of the compressible object is located inside the reservoir.

5. The device of any one of clauses 1-4, wherein the opening and the first end are connected with an air-tight and water-tight seal that includes the entire perimeter of the first hole.

6. The device of any one of clauses 1-5, wherein the compressible object comprises a shape and a material such that it will return to its uncompressed shape after the removal of a compressive force.

7. The device of any one of clauses 1-6, wherein an interior surface of the middle section adjacent to the second hole comprises one or more ribs dimensioned to receive and hold a ribbed tip of a catheter.

8. The device of any one of clauses 1-6, wherein an interior surface of the middle section adjacent to the second hole comprises threading dimensioned to receive and hold a threaded tip of a catheter.

9. The device of any one of clauses 1-6, wherein the middle section is dimensioned and configured to receive and hold a catheter through friction.

10. The device of any one of clauses 1-9, wherein the tubular member is located entirely inside the compressible object.

11. The device of any one of clauses 1-10, wherein the first end of the tubular member is located partially outside the compressible object.

12. The device of any one of clauses 1-11, wherein the surface of the compressible object has a Shore indentation hardness ranging from 50 to 90, as measured by the ASTM D2240 type A scale.

13. The device of any one of clauses 1-12, wherein compressing one side of the compressible object by 25% along an axis perpendicular to the tubular member results in a stiffness ranging from 0.5 pounds per inch to 5.0 pounds per inch.

14. The device of any one of clauses 1-13, wherein the compressible object can be elastically compressed along an axis perpendicular to the tubular member until it touches the tubular member without resulting in plastic deformation.

15. The device of any one of clauses 1-14, wherein the device does not comprise a valve.

16. The device of any one of clauses 1-15, wherein the only fluid communication between the lumen inside the compressible object and the space outside the compressible object is through the tubular member and the opening.

17. The device of any one of clauses 1-16, wherein the length of the tubular member ranges from 10% to 95% of the distance from the opening to an opposite side of the compressible object.

18. The device of any one of clauses 1-17, wherein the length of the tubular member ranges from 50% to 95% of the distance from the opening to an opposite side of the compressible object.

19. The device of any one of clauses 1-18, wherein the length of the tubular member ranges from 2 cm to 25 cm.

20. The device of any one of clauses 1-19, wherein the volume of the compressible object ranges from 10 ml to 500 ml.

21. The device of any one of clauses 1-20, wherein the compressible object has a length ranging from 5 cm to 50 cm.

22. The device of any one of clauses 1-21, wherein the compressible object has a width ranging from 2 cm to 20 cm.

23. The device of any one of clauses 1-22, wherein the ratio of the length to the width ranges from 0.9 to 3.0.

24. The device of any one of clauses 1-23, wherein the surface of the compressible object has a thickness ranging from 0.05 cm to 0.5 cm.

25. The device of any one of clauses 1-24, wherein the tubular member has a circular or oval cross section.

26. The device of any one of clauses 1-25, wherein the tubular member has a rectangular or square cross section.

27. The device of any one of clauses 1-26, wherein the compressible object comprises a wall comprising a plastic, a rubber, or a combination thereof.

28. A medical suction apparatus, comprising:
   a medical suction device of any of the preceding clauses; and
   a catheter comprising a distal end and a proximal end dimensioned to fit inside the tubular member.

29. The apparatus of clause 28, wherein one or more ribs located on an interior surface of the middle section and one or more ribs located on the proximal end of the catheter are dimensioned such that contact between the ribs will maintain the catheter inside the tubular member.

30. The apparatus of clause 28, wherein threading located on an interior surface of the middle section and threading located on the proximal end of the catheter are dimensioned such that contact between the threadings will maintain the catheter inside the tubular member.

31. The apparatus of any one of clauses 28-30, wherein the connection between the compressible object and the catheter is air-tight and water-tight.

32. The apparatus of any one of clauses 28-31, wherein the catheter comprises a Yankauer tip.

33. The apparatus of any one of clauses 28-32, wherein the catheter is curved.

34. A method of removing liquid from a throat of a subject, comprising:
positioning a medical suction apparatus according to any of the preceding clauses such that the distal end of the catheter is in contact with the liquid to be aspirated;
compressing the compressible object; and
releasing the compression on the compressible object, thereby aspirating at least some of the liquid from the throat into the compressible object.

35. The method of clause 34, wherein the compressing is performed before the positioning.

36. The method of any one of clauses 34-35, wherein the compressing is performed during or after the positioning.

37. The method of any one of clauses 34-36, wherein the compressing and releasing is performed by a single human hand.

38. The method of any one of clauses 34-37, wherein the compression is along an axis perpendicular to the tubular member.

39. The method of any one of clauses 34-38, further comprising compressing and releasing the compressible object a second time to aspirate additional liquid from the throat into the compressible object, wherein the distal end of the catheter remained within the throat between the first releasing and the second compressing.

40. The method of any one of clauses 34-39, wherein the distal end of the catheter was repositioned within the throat between the first releasing and the second releasing.

41. The method of any one of clauses 34-40, wherein the liquid is blood, mucus, saliva, or a combination thereof.

42. A kit comprising:
a medical suction device according to any of the preceding clauses; and
packaging containing the medical suction device.

43. The kit of clause 42, further comprising a catheter.

44. The kit of any one of clauses 42-43, wherein the catheter comprises a Yankauer tip.

45. The kit of any one of clauses 42-44, wherein the catheter is curved.

46. The kit of any one of clauses 42-45, wherein the medical suction device, and catheter if present, is sterile and the packaging is configured to keep the medical suction device sterile.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1: Medical Suction Apparatus and Use Thereof

As described above, a medical suction device includes an compressible object with an opening and a tubular member located inside the compressible object. The tubular member has a first end, a middle section, and a second end. The first end has a first hole located at the opening and the second end has a second hole. A space inside the compressible object is in fluid communication with a space outside the compressible object through the tubular member. FIGS. 1-9 show an exemplary embodiment of a medical suction device.

Figure 1:
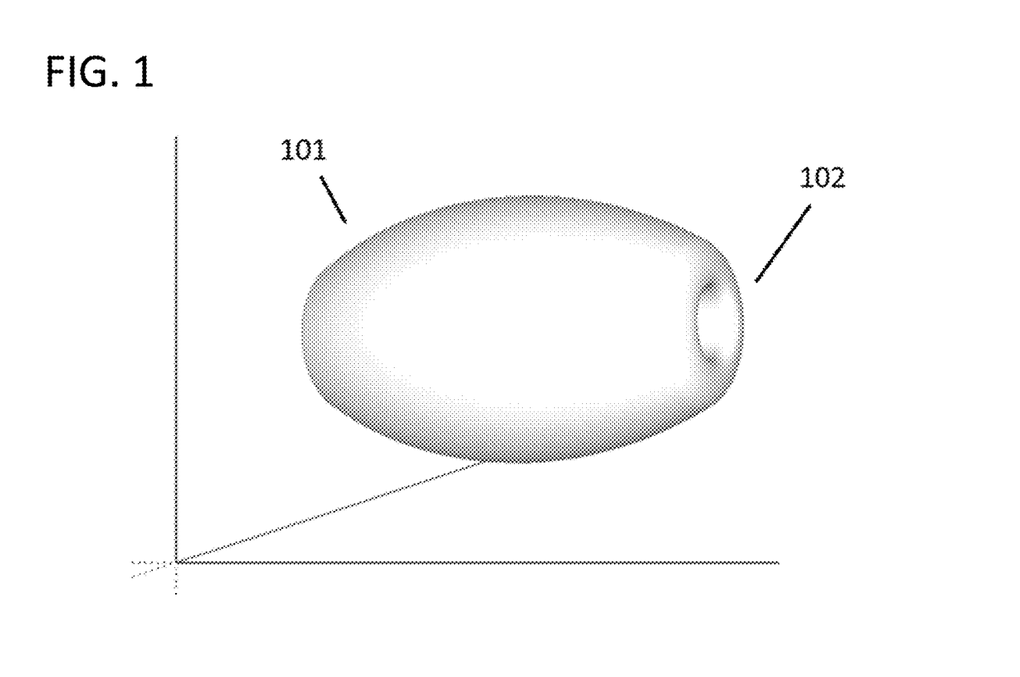
FIG. 1 shows a front perspective view of an exemplary medical suction device.

FIG. 1 shows a front perspective view of an exemplary medical suction device. The compressible object 101 and the opening in the compressible object 102 are shown.

Figure 2:
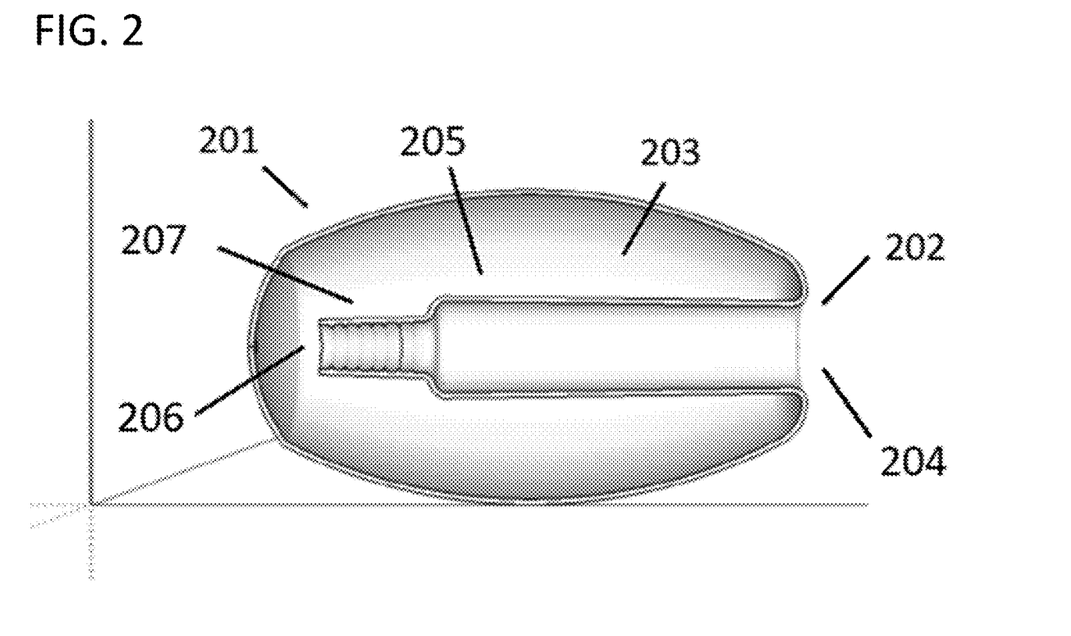
FIG. 2 shows a cross sectional view of the device.
Figure 3:
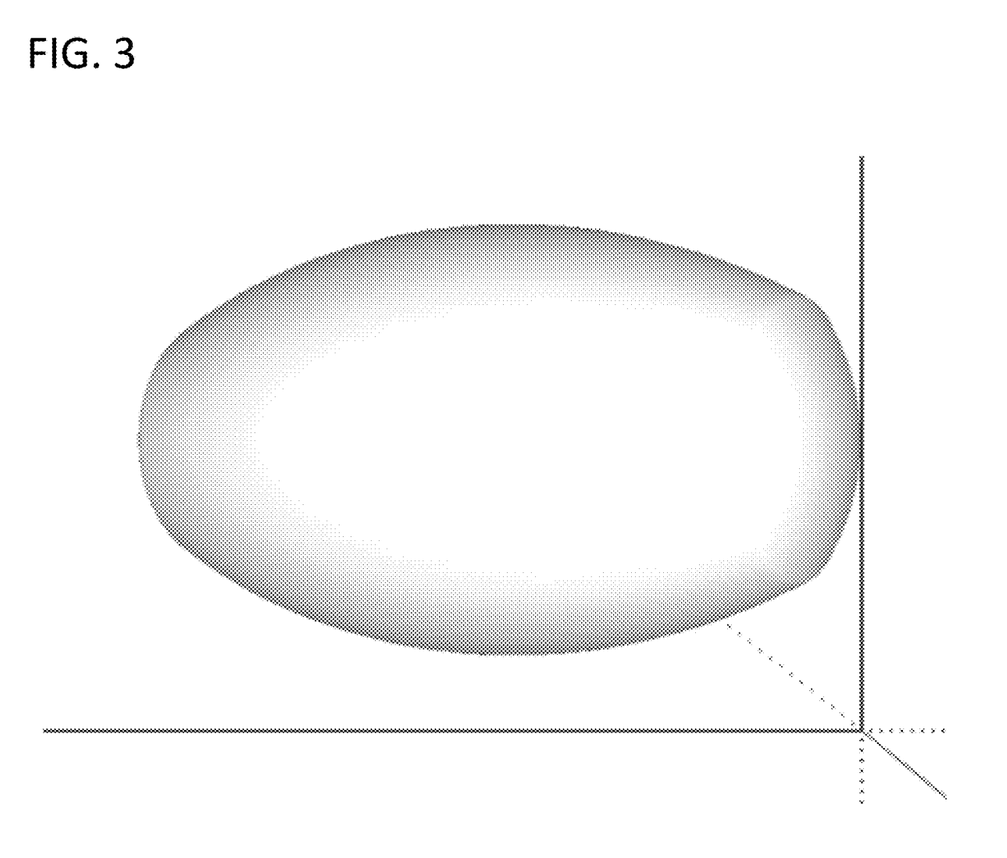
FIG. 3 shows a back perspective view of the device.
Figure 4:
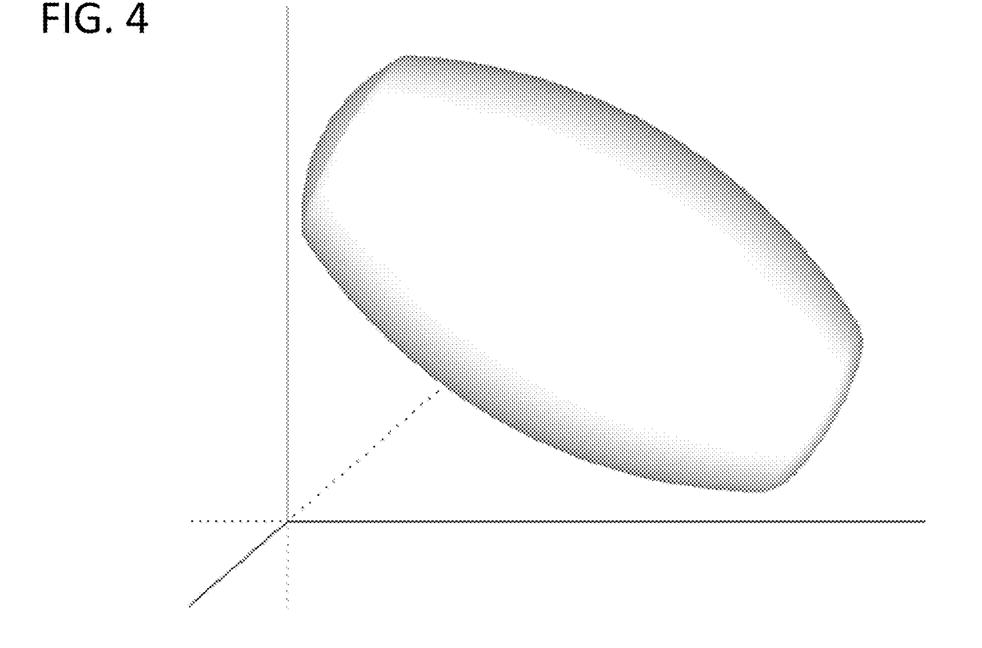
FIG. 4 shows a top perspective view of the device.
Figure 5:
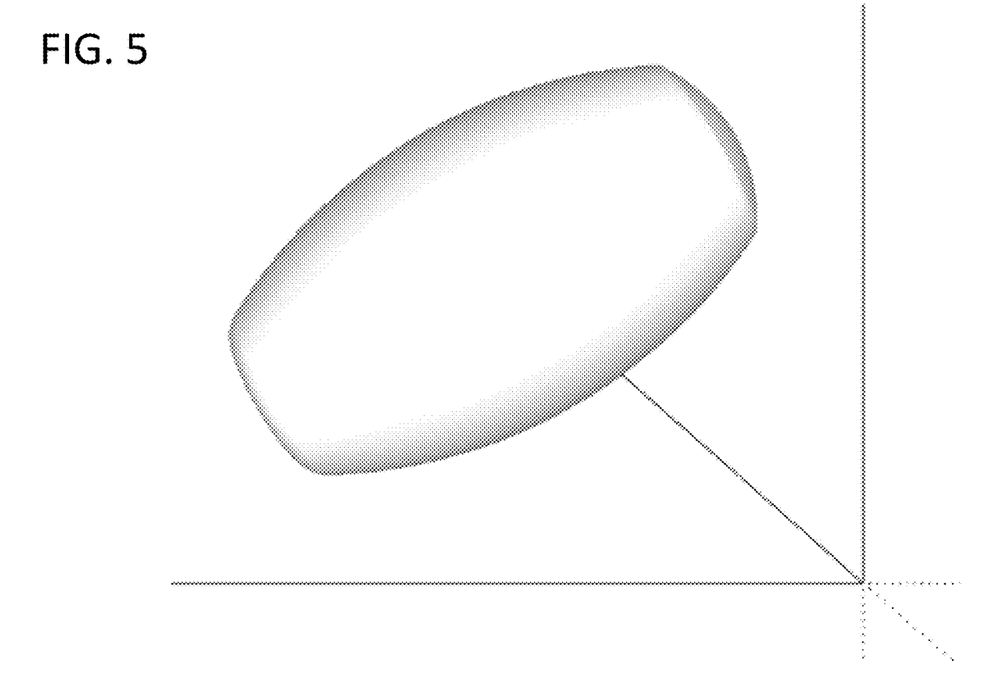
FIG. 5 shows a bottom perspective view of the device.
Figure 6:
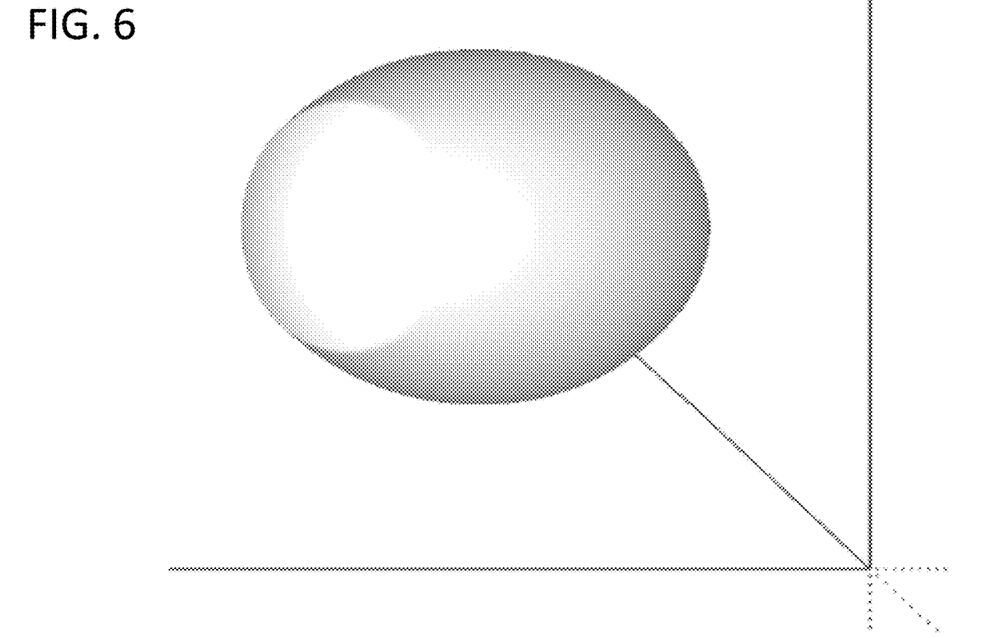
FIG. 6 shows a left perspective view of the device.

FIG. 2 shows a cross sectional view of the device. Compressible object 201 has opening 202 on the right side of the figure. Tubular member 203 has first end 204, middle section 205, and second end 206. First end 204 has a first hole located at the opening in the compressible object. Second end 206 has a second hole. Middle section 205 adjacent to the second hole is shown as having ribs 207 dimensioned to receive and hold a ribbed tip of a catheter.

FIGS. 3-6 shows back, top, bottom, and left perspectives view of the device wherein the opening is not visible.

Figure 7:
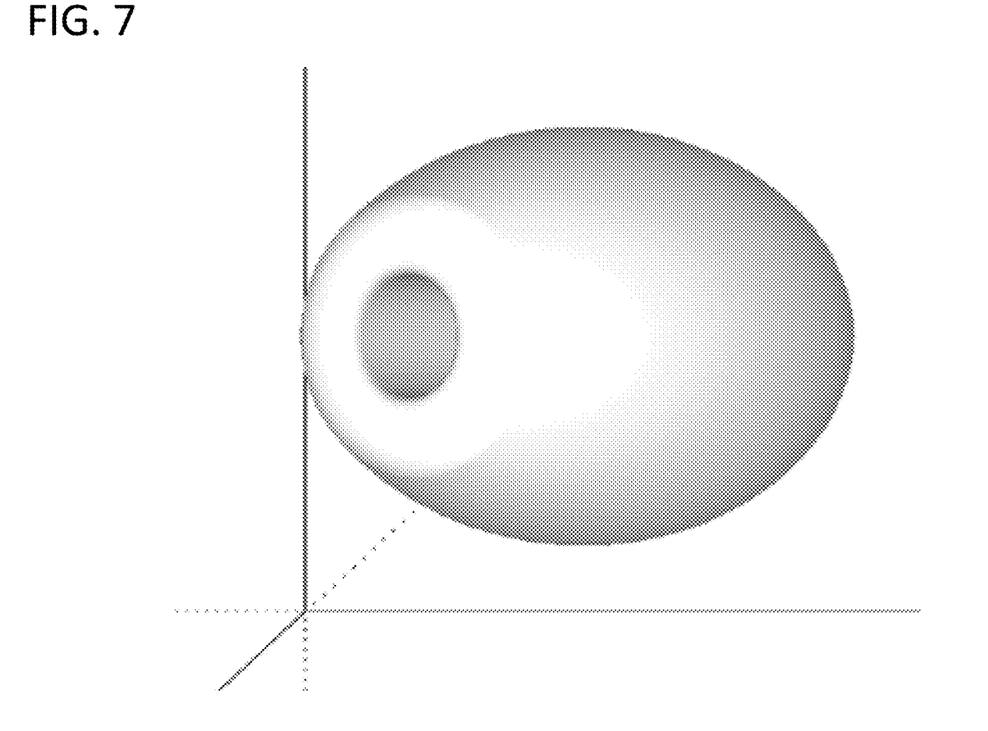
FIG. 7 shows a right perspective view of the device.

FIG. 7 shows a right perspective view of the device wherein the opening in the compressible object is visible. In addition, part of the tubular member is visible in this perspective.

Figure 8:
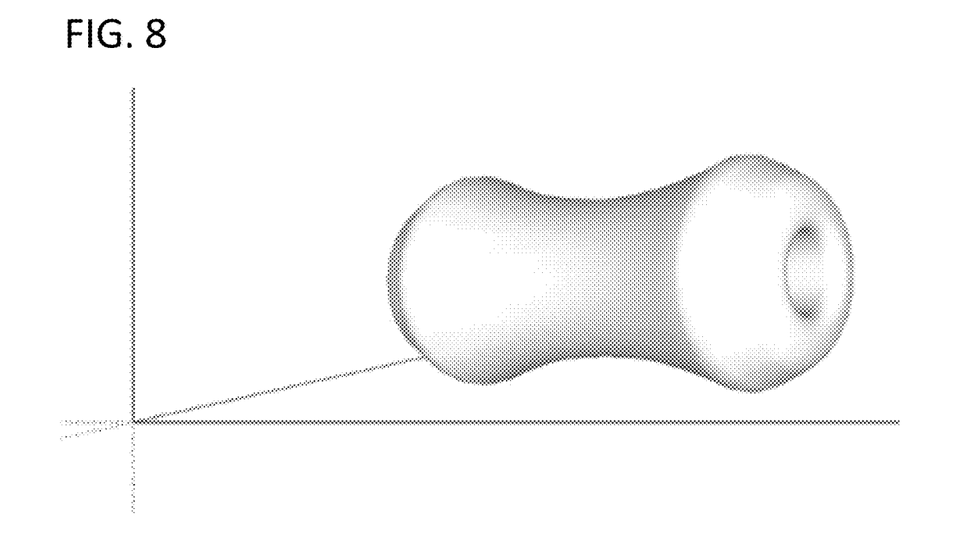
FIG. 8 shows a front perspective of the medical suction device compressed.

FIG. 8 shows the device in a compressed state. In this example, the compressible object is compressed along an axis that is perpendicular to the length of the tubular member. The length of the tubular member is an axis running from the first end to the second end of the tubular member.

Figure 9:
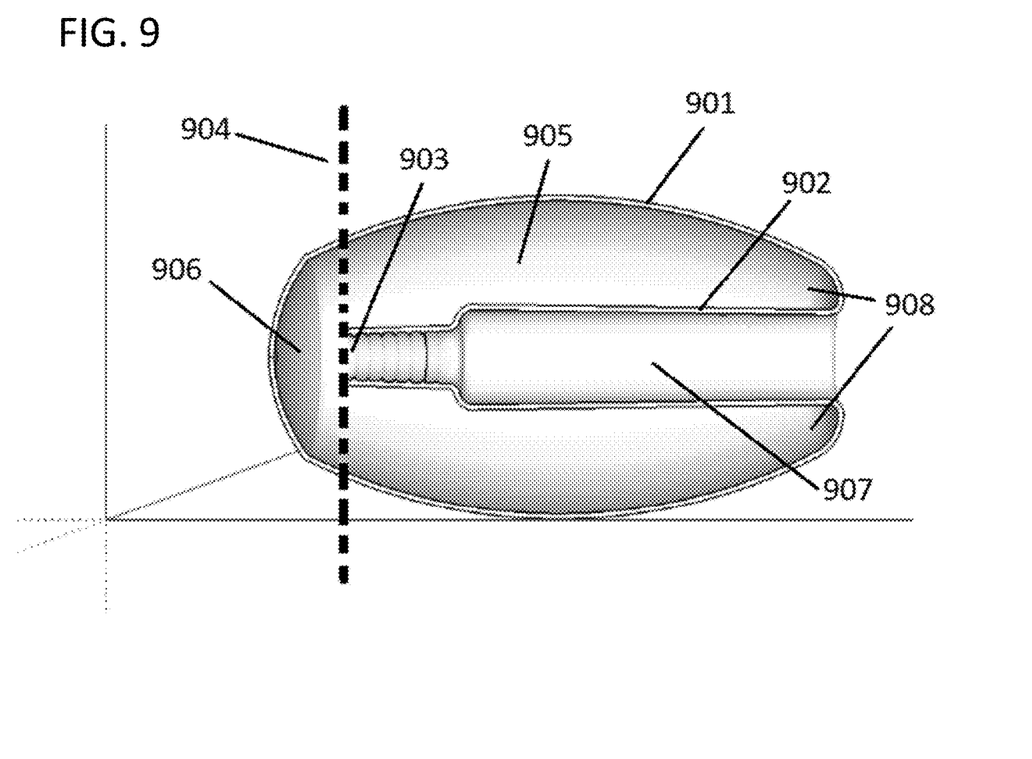
FIG. 9 shows a cross sectional view of the device denoting the reservoir.

FIG. 9 shows a cross sectional perspective denoting the reservoir. One of the boundaries of the reservoir 905 is plane 904, which is a plane containing second hole 903 and oriented perpendicularly to the tubular member, i.e., it is oriented perpendicular to an axis containing the first hole and the second hole. As such, the reservoir 905 is the space located between compressible object 901, middle section of the tubular member 902, and plane 904. Non-reservoir space 906 is the space outside the tubular member that is not part of the reservoir 905. In other words, non-reservoir space 906 is located between plane 904 and a part of the compressible object 901 opposite the opening. Stated in another manner, there is a volume inside the compressible object and outside the tubular member. The reservoir space 905 is the volume inside the compressible object and outside the tubular member that is not part of non-reservoir space 906. Also shown in FIG. 9 is tubular member space 907 which is located inside tubular member 902.

If the FIG. 9 device is rotated 90° clockwise, the opening in the compressible object will be pointed downwards. Thus, by compressing and then releasing the compressible object, liquid can be aspirated upwards, first through the compressible object opening, then through the tubular member 902, and finally through second hole 903. In such a case, the liquid will enter non-reservoir space 906, but due to the motion of the liquid and gravity, at least part of the liquid will continue moving into reservoir 905. In some cases, 90% or more of the aspirated liquid will move into reservoir 905, e.g. 99% or more. Due to gravity, the liquid will collect at reservoir end 908. Because the liquid becomes located in reservoir 905, compressing the compressible object an additional time will not cause the liquid to exit the compressible object. In other words, the particular spatial configuration of elements of the medical suction device allows for liquid to be aspirated into the device multiple times without the need to expel the liquid, e.g. into a waste container, between aspirations. In addition, since the reservoir is within the compressible object, it is possible for a user to operate the device using a single human hand.

In some cases, the only fluid communication between the space inside the compressible object and the space outside the compressible object is through the tubular member and the opening. For example, as shown in FIG. 9, the only fluid communication between reservoir 905 (and non-reservoir space 906) and the space outside the compressible object is through tubular member space 907, the opening, and the first hole. Using the terminology of the mathematical field of topology, holes can be referred to as either through-holes or blind-holes. In the FIG. 9 embodiment, the opening in the compressible object can be referred to as a blind-hole since the only fluid communication between the space inside the compressible object and the space outside the compressible object is through the opening. In other words, in the FIG. 9 embodiment, the compressible object has one blind-hole (i.e. the opening) and zero through-holes. It is noted that, in terms of the tubular member, the first hole and the second hole can be considered through-holes.

Figure 10:
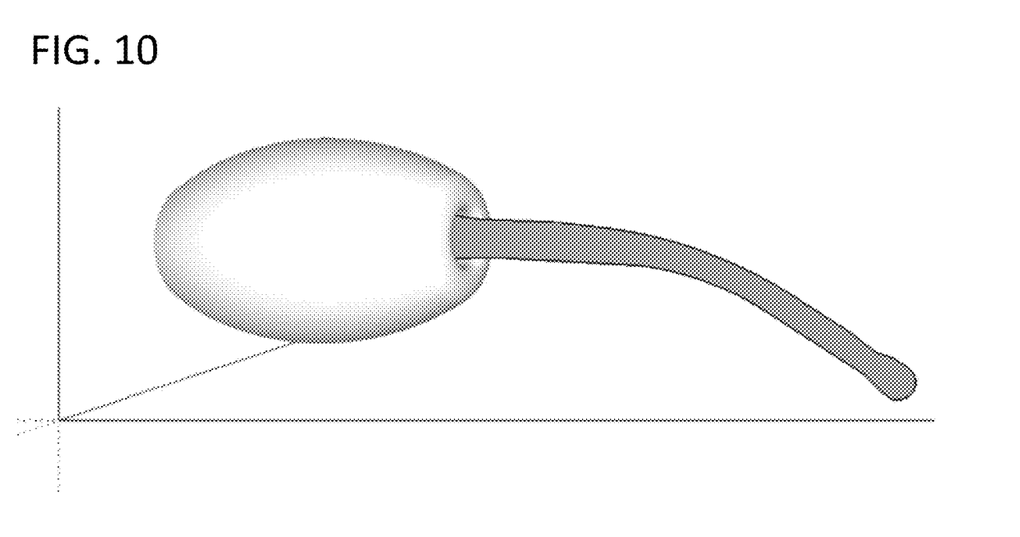
FIG. 10 shows a front perspective view of exemplary medical suction apparatus where a catheter is inserted into the medical suction device.
Figure 11:
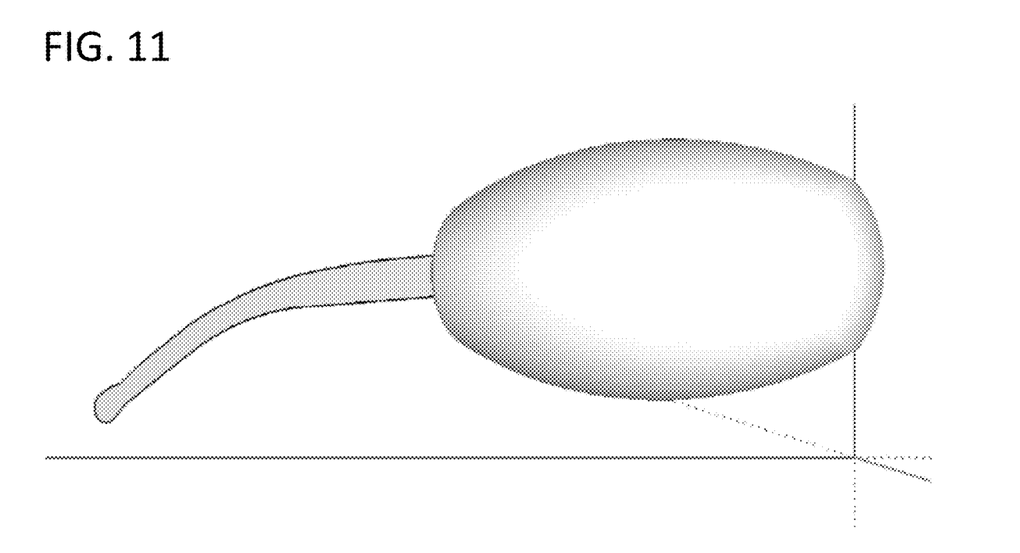
FIG. 11 shows a back perspective view of the apparatus.

FIGS. 10 and 11 show a front and back perspective of an exemplary medical suction apparatus. The apparatus includes a medical suction device as described above, along with a catheter inserted into the device.

Figure 12:
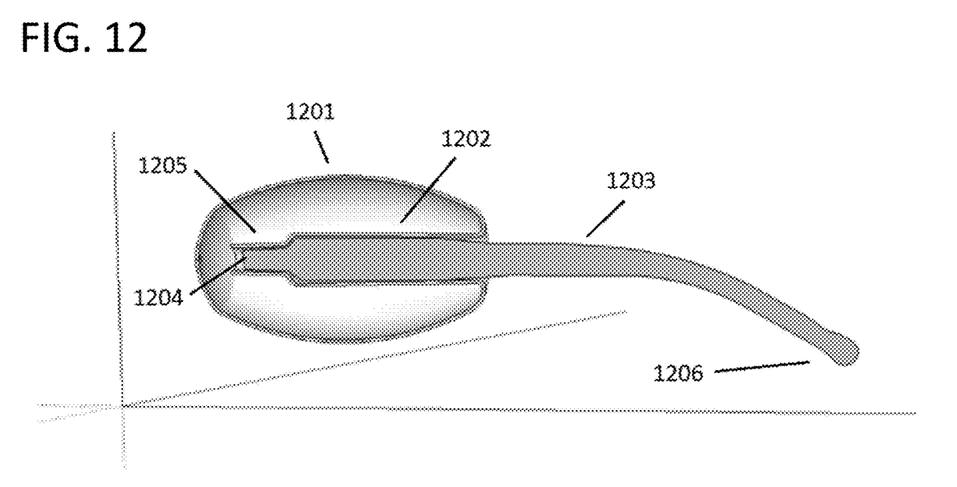
FIG. 12 shows a cross section view of the apparatus.

FIG. 12 shows a cross sectional view of the apparatus. As described before, the device includes compressible object 1201 and tubular member 1202. The catheter 1203 includes a ribbed end 1204 that is dimensioned to interact with ribs 1205 of the tubular member such that the catheter is retained inside the device. Catheter 1203 is curved. Catheter 1203 also includes a bulbous tip 1206. The terms bulbous tip and Yankauer tip are used interchangeably herein.

Figure 13:
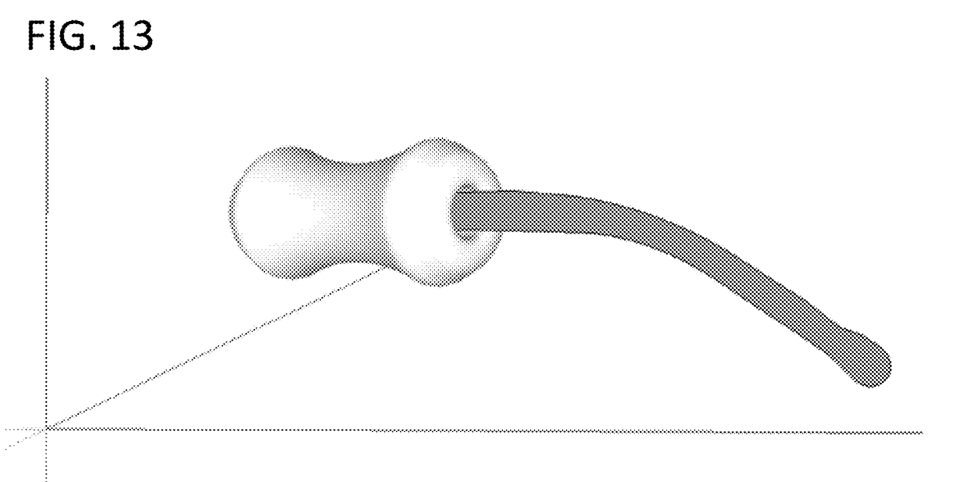
FIG. 13 shows a front perspective of the medical suction apparatus compressed.

FIG. 13 shows a front perspective of the apparatus while the compressible object is being compressed.

What is claimed is:

1. A medical suction device, comprising:
a compressible object; and
a tubular member located inside the compressible object and comprising a first end, a middle section and a second end,
wherein the first end comprises a first hole located at the opening and the second end comprises a second hole,
wherein the compressible object comprises:
(i) a surface;
(ii) an opening in the surface;
(iii) an internal lumen completely defined by the surface and the opening;
(iv) a reservoir comprising a first space; and
(v) a non-reservoir space located between a part of the compressible object opposite the opening and a plane containing the second hole and oriented perpendicular to the tubular member,
wherein an interior surface of the middle section adjacent to the second hole comprises: (i) one or more ribs dimensioned to receive and hold a ribbed tip of a catheter, or (ii) threading dimensioned to receive and hold a threaded tip of a catheter,
wherein the first space is located between the surface of the compressible object and the middle section,
wherein the first space is located between the surface of the compressible object and the plane containing the second hole and oriented perpendicular to the tubular member,
wherein the first space is located between the middle section and the plane containing the second hole and oriented perpendicular to the tubular member,
wherein the lumen of the compressible object is in fluid communication with a second space outside the compressible object through the tubular member, and
wherein the opening is a blind hole.

2. The device of claim 1, wherein the opening and the first end are connected with an air-tight and water-tight seal that includes an entire perimeter of the first holes.

3. The device of claim 1, wherein the compressible object comprises a shape and a material such that it will return to an uncompressed shape after the removal of a compressive force.

4. The device of claim 1, wherein an interior surface of the middle section adjacent to the second hole comprises one or more ribs dimensioned to receive and hold a ribbed tip of a catheter.

5. The device of claim 1, wherein the tubular member is located entirely inside the compressible object.

6. The device of claim 1, wherein the device does not comprise a valve.

7. The device of claim 1, wherein a length of the tubular member ranges from 50% to 95% of the distance from the opening to an opposite side of the compressible object.

8. The device of claim 1, wherein the tubular member has a circular or oval cross section.

9. A medical suction apparatus, comprising:
the medical suction device of claim 1; and
a catheter comprising a distal end and a proximal end dimensioned to fit inside the tubular member.

10. The apparatus of claim 9, wherein one or more ribs located on an interior surface of the middle section and one or more ribs located on the proximal end of the catheter are dimensioned such that contact between the ribs will maintain the catheter inside the tubular member.

11. The apparatus of claim 9, wherein the connection between the compressible object and the catheter is air-tight and water-tight.

12. The apparatus of claim 9, wherein the catheter comprises a Yankauer tip.

13. A method of removing liquid from a throat of a subject, comprising:
- positioning the medical suction apparatus according to claim 9 such that the distal end of the catheter is in contact with the liquid to be aspirated;
- compressing the compressible object; and
- releasing the compression on the compressible object, thereby aspirating at least some of the liquid from the throat into the compressible object.

14. The method of claim 13, wherein the compressing and releasing is performed by a single human hand.

15. The method of claim 13, further comprising:
- compressing the compressible object a second time; and
- releasing the compressible object a second time to aspirate additional liquid from the throat into the compressible object,
- wherein the distal end of the catheter remained within the throat between the releasing and the compressing the second time.

16. The method of claim 15, wherein the distal end of the catheter is repositioned within the throat between the first releasing and the second releasing.

17. A kit comprising:
- the medical suction device according to claim 1; and
- packaging containing the medical suction device.

18. The device of claim 1, wherein 25% to 95% of the volume inside the compressible object is located inside the reservoir.

19. The device of claim 1, wherein the reservoir has a volume ranging from 10 ml to 750 ml.

20. The device of claim 1, wherein the second hole is oriented perpendicular to the tubular member.

21. The device of claim 1, wherein an interior surface of the middle section adjacent to the second hole comprises threading dimensioned to receive and hold a threaded tip of a catheter.

22. The device of claim 1, wherein the tubular member has a circular cross section.

23. The device of claim 1, wherein the first end, the middle section, and the second end of the tubular member each have a circular cross section.

24. The device of claim 1, wherein the second hole has a circular cross section.

25. The device of claim 1, wherein the second hole is located entirely within the plane containing the second hole and oriented perpendicular to the tubular member.

* * * * *